(12) United States Patent
Lazo et al.

(10) Patent No.: US 7,475,087 B1
(45) Date of Patent: Jan. 6, 2009

(54) COMPUTER DISPLAY TOOL FOR VISUALIZING RELATIONSHIPS BETWEEN AND AMONG DATA

(75) Inventors: Gerard R. Lazo, Hercules, CA (US);
Nancy Y. Lui, San Francisco, CA (US);
Frank M. You, Albany, CA (US)

(73) Assignees: The United States of America as represented by the Secretary of Agriculture, Washington, DC (US);
Washington State University Research Foundation, Pullman, WA (US)

( * ) Notice: Subject to any disclaimer, the term of this patent is extended or adjusted under 35 U.S.C. 154(b) by 286 days.

(21) Appl. No.: 10/734,366

(22) Filed: Dec. 12, 2003

Related U.S. Application Data

(60) Provisional application No. 60/498,840, filed on Aug. 29, 2003.

(51) Int. Cl.
*G06F 7/00* (2006.01)
*G06F 17/00* (2006.01)
(52) U.S. Cl. .................................. 707/102; 707/104.1
(58) Field of Classification Search ...................... 707/3, 707/6, 104.1; 435/6; 706/50
See application file for complete search history.

(56) References Cited

U.S. PATENT DOCUMENTS 5,832,182 A * 11/1998 Zhang et al. .................. 706/50
6,449,612 B1 * 9/2002 Bradley et al. ................. 707/6
6,522,782 B2 2/2003 Pass et al.
6,567,540 B2 5/2003 Balaban et al.
6,629,097 B1 9/2003 Keith
6,631,331 B1 10/2003 Sabry et al.
6,633,819 B2 10/2003 Rzhetsky et al.
6,651,008 B1 11/2003 Vaisberg et al.
6,920,450 B2 * 7/2005 Aono et al. ..................... 707/3
7,047,255 B2 * 5/2006 Imaichi et al. ........... 707/104.1
2004/0121360 A1 * 6/2004 Karchi et al. ................... 435/6

OTHER PUBLICATIONS

Kumar, S., et al., "Best: A Novel Computational Approach for Comparing Gene Expression Patterns From Early Stages of *Drosophila melanogaster* Development," (2002) *Genetics* 162:2037-2047.

(Continued)

*Primary Examiner*—Etienne P LeRoux
*Assistant Examiner*—Paul Kim
(74) *Attorney, Agent, or Firm*—Elizabeth R. Sampson; David R. Nicholson; John D. Fado

(57) ABSTRACT

The invention is directed to a tool for visualizing relationships between and among data. It uses existing relational databases, and provides the means to view these databases in order to reveal degrees of relatedness between and among various data clusters. An illustrative use of said database tool is for analyzing genomics data. A test platform for this tool used EST data for the wheat tribe Triticeae, but can easily be extended for applications where other sequence assembly procedures are implemented, particularly those which use alphanumeric characters to represent data. The implementation of algorithms to manipulate the data points for investigative functions may be adapted to serve other applications.

8 Claims, 9 Drawing Sheets
(7 of 9 Drawing Sheet(s) Filed in Color)

OTHER PUBLICATIONS

Kaminski, N., "Bioinformatics A User's Perspective," (2000) *Am. J. Respir. Cell Mol. Biol.* 23:705-711.

Aravind, L. and Koonin, E.V., "Gleaning Non-trivial Structural, Functional and Evolutionary Information About Proteins by Iterative Database Searches," (1999) *J. Mol. Biol.* 287:1023-1040.

Lazo, G., N. Lui, F.M. You, D.D. Hummel, S. Chao, and O.D. Anderson, "Charting Contig-Component Relationships within the Triticeae," In: Genome Exploration: Data Mining the Genome (2005) Chapter 8 pp. 109-120 Springer Science+Business Media Publishing, Inc. New York, NY.

* cited by examiner

Only Gliadin Contigs Highlighted

Only Gliadin Contigs Highlighted

COMPUTER DISPLAY TOOL FOR VISUALIZING RELATIONSHIPS BETWEEN AND AMONG DATA

This is an application for a utility patent, filed pursuant to 35 U.S.C. § 111(a).

CROSS-REFERENCE TO RELATED APPLICATION

This application relates to and claims benefit of Provisional Patent Application No. 60/498,840, filed on Aug. 29, 2003, all of which disclosure is incorporated herein by reference.

REFERENCE TO APPENDIX

This application includes an appendix containing computer programming code, provided in both written and CD-ROM form, all of which is incorporated herein by reference.

BACKGROUND OF THE INVENTION

The present invention relates to the fields of relational databases, database use, graphical presentation of data, genomics, and gene discovery.

Relational databases continue to grow in number and complexity. Making sense of the data contained in these databases similarly is becoming a more daunting task. The data in these databases are often packaged or tagged in alphanumeric form in order to facilitate their handling and sorting. Examples of this can be found in many of the databases that contain chemical and biological information, such as Expressed Sequence Tags, or ESTs. In fact, the databases in this field provide a good example and are illustrative of the general problem that has arisen in database management, namely, how a researcher can effectively use the massive amount of information that is available.

Research into gene discovery, for example, often focuses on ESTs which in general reflect the diversity of gene expression in living organisms.

These sequences result from an established path in the laboratory: pieces of single-stranded messenger ribonucleic acid (mRNA) are isolated from organic tissue, converted into double-stranded complementary deoxyribonucleic acid (cDNA), cloned into vector replicons, and then transformed into *Escherichia coli* or other expression systems for replication. Deoxyribonucleic acid (DNA) is extracted from these clones and sequenced using high-throughput methods resulting in pools of EST data (Adams et al., 1992, Sequence Identification of 2375 Human Brain Genes, Nature 355:632-34). Such methods mean that a given set of sequences, often called a "library", shares a common origin, i.e., they have the same species, cultivar, tissue, condition, and stress attributes. Their characteristics represent a snapshot of the organism, captured at the moment in time when the researcher isolated the mRNA.

The abundance of EST data has increased dramatically in the past few years. The plant tribe Triticeae, for example, includes several closely-related crop plants of major economic importance, including wheat, barley and rye (Barkworth et al., 1992, Taxonomy of the Triticeae, A Historical Perspective, Hereditas 116:1-14; and Kellogg, 2001, Evolutionary History of the Grasses, Plant Physiology 125:1198-1205.) In the year 1998, only a handful of ESTs from *Triticum* sp. plants were available; now the number of ESTs for *Triticum* sp. exceed 750,000 (NCBI dbEST, 2003). This information has been assembled into vast databases, which are growing exponentially from year to year.

How to manage such massive amounts of data is difficult and labor intensive. For example, to help process this overload of information and to remove redundancy from within an EST data set, sequences can be aligned and clustered using various assembly algorithms, some of the more popular being CAP3 (Huang and Madan, 1999, CAP3: A DNA Sequence Assembly Program, Genome Res. 9:868-877), phrap (Green, 2003, The Phrap Program, www.phrap.org) and d2_cluster (Burke et al., 1999, D2 Cluster: a Validated Method for Clustering EST and Full-Length cDNA Sequences, Genome Res. 9:1135-1142). Moreover, in building such an assembly, a set of unique gene sets can be assembled into "unigenes", essentially representing a range of genes present in an organism (Liang et al., 2000, An Optimized Protocol for Analysis of EST Sequences, Nucleic Acids Res. 28:3657-65; and Quakenbush et al., 2000, The TIGR Gene Indices: Reconstruction and Representation of Expressed Gene Sequences, Nucleic Acids Res. 28:141-45). The success of such an assembly relies on the quality of the sequence data and the various parameters available within the software used to provide the established settings for sequence-by-sequence comparisons, all of which has become quite difficult because of the sheer mass of information that must be evaluated and processed.

As these databases have grown larger and larger, the amount of time and labor needed to use them has also grown. What is needed is a type of search and analytical tool that can be used with large databases in general, and particularly those which use alphanumeric characters to identify underlying information. In other words, virtually all databases.

SUMMARY OF THE INVENTION

An analytical tool has been developed to complement database use and analysis. It can be used with existing databases by providing an overall visual representation of data that are gathered and clustered by common attributes. Moreover, the tool permits the researcher to see relationships among the data that would otherwise have been difficult or impossible to see.

The database tool interacts with a relational database to point to other relevant pieces of information. Rather than having to develop specific questions to query a relational database, the display produces a global perspective of the data set and allows orienting decisions based on attributes of the contributing data variables, allowing the observer to make intuitive research decisions based on the clustering patterns of the data elements.

Data points may be selected individually or collectively to follow in-depth information associated with the data points. With this tool it is possible to pose a wide range of queries based on known data point features such as those relating to library origin, metabolic pathway, map position, and the like. The sorting classes in the display make use of information tied to the classes which provide points of reference based on selected calculations which otherwise, would not be easily detectable from a standard text-based database query.

Visualization of the data analysis augments conventional use of existing database information by providing a different perspective of the data set, and by providing an interface by which to view and query the data. In other words, the invention is a database tool that goes beyond a simple listing of query results. This tool provides the user with the opportunity to explore existing databases in a new way that is both intuitive and graphically revealing.

An illustrative use of the tool is with gene discovery efforts. In this embodiment, the tool is called the Contig Constellation Viewer, or CCV.

This analytical tool has also been modified to interact with data for microarray expression analysis, and to aid phylogenetic determination of genome sequences.

BRIEF DESCRIPTION OF THE DRAWINGS

Please note that the analytical tool which is the subject of this application is directed to a graphical display which depends, in part, on the use of color. Color drawings are therefore necessary in order to understand the operation of the invention, and the application contains at least one drawing executed in color. Copies of the patent or published patent application with color drawings will be provided by the Office upon request and payment of the necessary fee.

FIG. 3 shows a sample contig point (number 8694) which appears in the upper right text box in the figure. The numbers highlighted around the periphery indicate the number of EST members from each library that are associated with contig point 8694. From contig point 8694, lines radiate to the libraries which contributed to the point, while the other points remain as non-annotated points.

In FIG. 5($a$) the libraries are sorted by "tissue-type" and in FIG. 5($b$) the libraries are sorted based on "development stage." Other sorting attributes can include such categories as "species," "cultivar," "stress condition," "germplasm," and "conditional state/treatment." As an example of how the display tool can be used to identify contigs with particular attributes, highlighted in red in each figure are contig points which have the best homology matching to "gliadin." This example also shows that known genes can be highly associated with specific tissue types (FIG. 5($a$)) and specific developmental stage expression (FIG. 5($b$)).

DEFINITIONS

Figure 1:
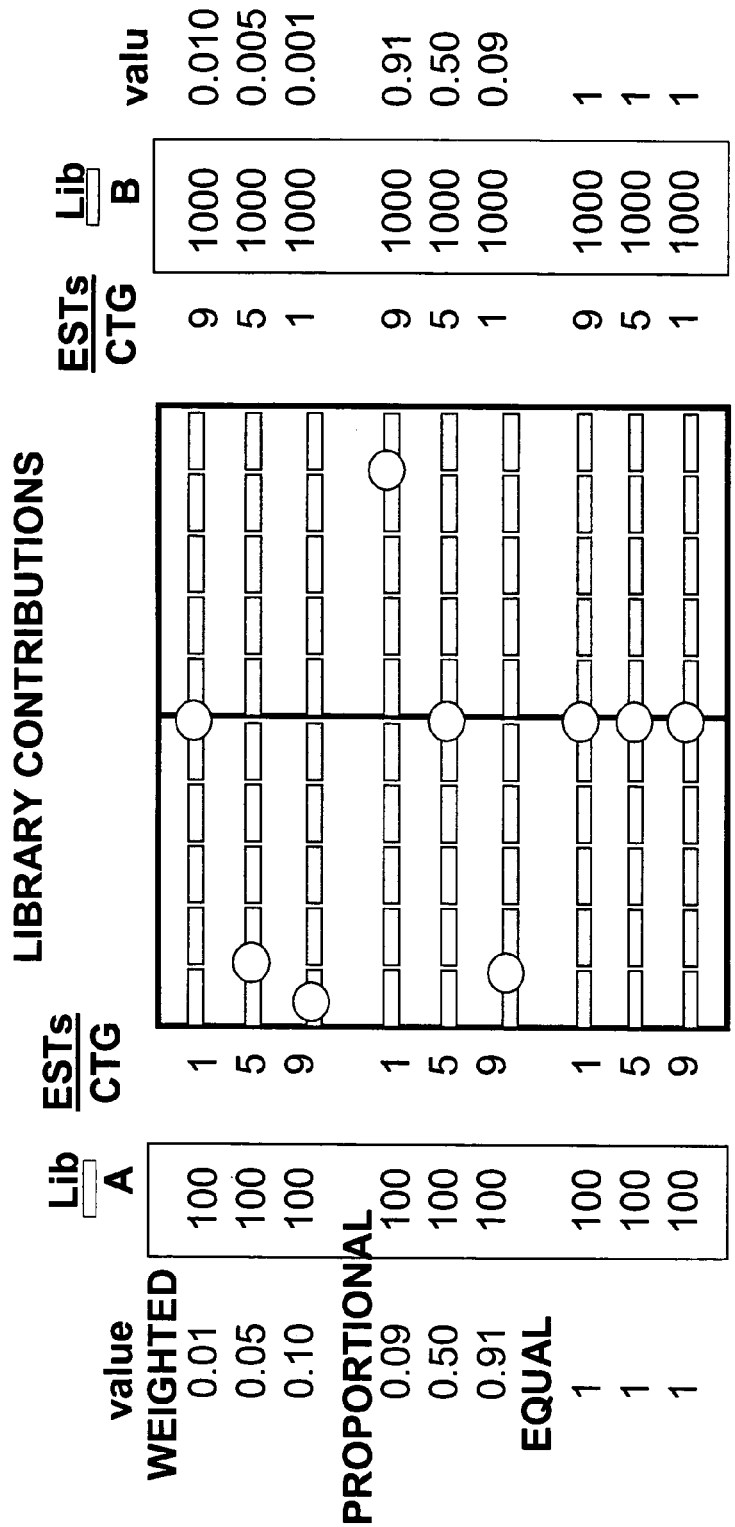
FIG. 1 is a chart demonstrating the difference between the settings of equal, proportional, and weighted.

Unless defined otherwise, all technical and scientific terms used herein have the meaning as set forth in the following textbooks: Lodish, et. al., Molecular Cell Biology ($5^{th}$ ed. 2003), and Nelson, D., and Cox, M., Lehninger Principles of Biochemistry (3rd ed. 2000).

EST is an abbreviation for "expressed sequence tag" and refers to a DNA sequence derived by sequencing an end of a random cDNA clone from a library of interest.

CONTIG is a data point which represents a consensus string created from comparing subset sequence data using assembly algorithm programs. CONTIG also refers to a DNA sequence assembled from overlapping shorter sequences to form one large contiguous sequence.

"Assembly" is the process used to build contigs.

"Library" includes, but is not limited to, collections of gene sequences, protein sequences, and any collection of data that may be identified in alphanumeric form or any variation thereof.

"Alphanumeric" refers to the representation of data by any combination of letters and/or numbers.

"MYSQL" is an open source relational database management system (RDBMS) that uses Structured Query Language (SQL), a popular computer language for adding, accessing, and processing data in a database. It uses kernel multi-threads, and provides application program interfaces (APIs) for C, C++, Eiffel, Java, Perl, PHP, Python, and Tcl.

"JAVA" is a programming language expressly designed for use in the distributed environment of the Internet. It was designed to have the "look and feel" of the C++ language, but it is simpler to use than C++ and enforces an object-oriented programming model. Java can be used to create complete applications that may run on a single computer or be distributed among servers and clients in a network. It can also be used to build a small application module or applet for use as part of a Web page. Applets make it possible for a Web page user to interact with the page.

"APPLET" refers to a small program that can be sent along with a Web page to a user. Java applets can perform interactive animations, immediate calculations, or other simple tasks without having to send a user request back to the server.

"ENTREZ" is the search and retrieval system that integrates information from the National Center for Biotechnology (NCBI) databases. These databases include nucleotide sequences, protein sequences, macromolecular structures, whole genomes, and MEDLINE, through PubMed.

"TOMCAT" is an open source implementation of Java Servlet and JavaServer Pages technologies.

"APACHE" is a freely available Web server that is distributed under an "open source" license. It runs on most Unix-based operating systems (such as Linux, Solaris, Digital UNIX, and AIX), on other UNIX/POSIX-derived systems (such as Rhapsody, BeOS, and BS2000/OSD), on AmigaOS, and on Windows 2000.

DETAILED DESCRIPTION OF THE INVENTION

The disclosed invention is an analytical tool that permits the plotting, visualization, and manipulation of data variables, particularly as those data points cluster according to common attributes. The tool allows for the manipulation of the display of data in a manner that permits the viewer to draw conclusions about data relationships that would otherwise not be possible or apparent.

One embodiment of the invention, called the Contig Constellation Viewer (CCV), is for use in the study of EST data. It is an analytical tool that permits the visualization and manipulation of data variables related to cDNA libraries and their contributions toward assembled contigs.

Much of the genome sequence data needed for research is often housed in relational databases and can be readily retrieved, but generally only in a form or in response to a query that has been somewhat predetermined by the curators of the databases. From an object or relational database perspective, the data is therefore of somewhat limited use since it can be viewed only in response to specific, pre-determined queries posed directly to the database. Furthermore, in consideration of the enormous amount of EST information available, curators of these databases are faced with the daunting task of trying to anticipate those queries or attributes which are most important to or most-often sought by the researcher, and to fashion appropriate queries in order to present sequence or database library information in a coherent manner. To this end, curators endeavor to conceive of the most probable queries, but it is unavoidable that not every possible query can be anticipated.

The CCV application presented here permits a global visualization of library data in a spatial array using a multi-dimensional display. It can be further queried in various ways making use of its links to a relational database, permitting the data to be viewed from a variety of perspectives which will permit the inference of relatedness between and among the source libraries providing the data clusters being displayed. It gives the researcher the ability to see data and make comparisons that are not possible when using the predetermined queries that are common with existing databases.

The CCV tool provides an overview of the available data. By ranking the library attributes by criteria of interest to the researcher, it provides an intuitive interface that will help the researcher focus on those sequences or candidates that may be most applicable to the research needs. The setup of the CCV interface gives the researcher an overview of all available data in an assembly study and relates it to a collection of attributes believed to be useful in sorting the data. The graphical interface simplifies the ability to create queries and provides an interface to make general observations and develop new queries. The interface uses one assembly and uses contigs for studying sequences based on their derived origins.

Considering, for example, that the over 780,000 sequences representing the tribe Triticeae are derived from only 256 cDNA libraries, it is still unclear to what extent the expressed portion of the genome is represented. It is possible to gauge these numbers from model organisms with sequenced genomes, but even in these cases, the numbers are still unclear.

In surveying the expression association patterns with some of the Triticeae assemblies, it is apparent that ESTs fall short of representing the full diversity of expressed genes possible. For example, sequences from a cDNA library derived from callus tissue in barley were found to have a high number of EST sequences in contigs that were apparently callus-specific. Many of the sequences here were apparently unique from those expressed in other tissues. This suggests that an abundance of sequences derived from callus have not been detected under classic mRNA conditional states of isolation.

It is also suggested here that callus-derived tissues may relate to a state where inhibitions or regulation of mRNA transcription are released or not controlled, allowing a diversity of sequences to be expressed and detected, except out of context with respect to tissue, development, and the like. Sequences of this sort may simply define the state of callus expression.

From the above simple, illustrative observation, there still appears to be value in sequencing additional cDNA libraries under a wider range of expression profiles. This would add additional value to the cDNA libraries by enabling the tracking of added attributes, or variables, such as species, germplasm, tissue, developmental stage, and stresses. Establishing new unstudied conditions for the production of cDNA libraries would be useful for coaxing a genome to express sequences important to different states of being, including relationships to developmental stage, stresses, or tissue types.

The computational design and computer program presented here is intended to condense large datasets into a manageable and discernable environment using visualization methods. This approach is different in that contigs can be viewed based on their sequence construction from assembly algorithm programs, allowing each contig to be related in context to other assembly contigs based on their sources and attributes.

The end result is a multi-dimensional color display of the assembly experiment, with the ability to study and manipulate the data clusters that are formed by connecting to an accompanying relational database. Moreover, a subset of the assembly can be displayed to uncover various interactions. The global visualization in many cases simplifies access to the data that normally would require several directed queries to uncover the same information. In other cases the visualization provides a display that prompts the user to intuitively query for data, which would not be obvious starting from a "command-line" type query.

The orientation of contigs displayed is dependent on the sorting order and the algorithm utilized to represent the display. With the sampled assemblies, up to 50,000 contigs were represented at a time with the visualization tool. The patterned layout of contigs in the CCV display would provide an intuitive means to focus on contigs representing interests for the researcher.

To relate to potential expression profiles, for example, the libraries can be sorted based on, but not limited to, species, cultivar, tissue, developmental stage, or conditional state/stresses. Clustering patterns would reflect those contigs with an abundance of ESTs important for the different sorted criteria.

The primary software interface is a Java applet (Java, 2003), which interacts with information housed in a relational database. The relational database that was used, mySQL (MySQL, 2003), houses the relevant information for relating contigs to components of associated libraries. Supplemental information for contigs and their sequences are also served through the relational database.

Figure 7:
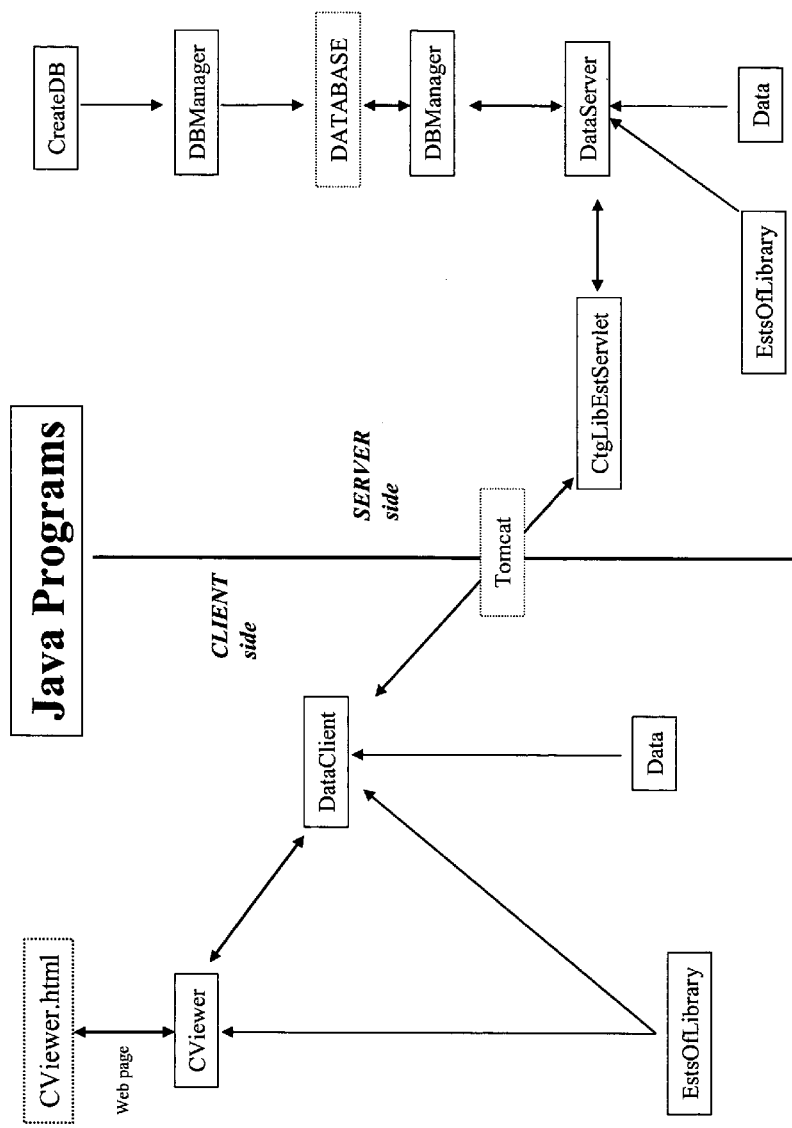
FIG. 7 is a flow chart and schematic showing the relationship of the client server network and further elucidating the problem solving/data building process as applied to one specific application of the invention, namely comparing ESTs from a plurality of EST libraries.

For convenience, a Java applet can be used and served through an Internet browser interface as a client application. On the server side, a Java servlet can be queried through a web server, such as Apache (Apache, 2003), to retrieve data from the relational database. See FIG. 7 and Appendix A. For each assembly to be set up for study, a protocol can be established for uploading the data sets. See FIG. 7 and Appendix A. An example of such a protocol is presented in the "examples and illustrations" section below. The Apache Tomcat servlet container is used to allow the flow of data from the relational database to the software applet.

From the assembly data, key information is gathered for each of the sequences to build the attribute lists for each sequence data point, starting with the cDNA library origin, and then to follow up on the attributes of each library for other attributes such as, but not limited to, species, germplasm, tissue, developmental stage, and conditional state/stresses information.

A library information and sequence file is created using program scripts written in PERL for publicly available or customized sequence repository databases. The PERL scripts are also used to parse out the results from an assembly process. Then the assembly lists are created for "library codes", "contigs", and the "sequence accession/associated contig/library affiliation" associations. An example of how these scripts can be put together is provided in the "examples and illustrations" section found below.

Three different display algorithm settings can be applied, termed: equal, proportional, and weighted. See FIGS. 1-4. Each setting can be used to view contig data from the EST libraries placed around the periphery of the multi-dimensional graphical display (or "figure") from different perspectives. Examples of how these settings can be used are also set forth below.

The differences in these display settings (equal, proportional, weighted) is due to how the differently applied algorithms (equal, proportional, weighted) affect placement of contigs within the display. See FIGS. 1-4.

Because libraries represented in the CCV display can be sorted based on key library components, or attributes, the display can be geared towards uncovering the way contigs associate with these key attributes. Since contigs patterned as simple intersections between libraries may not adequately explain contig-component relationships, other algorithm settings can be used. Following are a few case studies representing a range of applications.

EXAMPLES OF USE AND ILLUSTRATIVE APPLICATIONS

The following examples are intended only to further illustrate the invention and are not intended to limit the scope of the invention which is defined by the claims. These examples relate to the embodiment of the invention known as the CCV, or Constellation Contig Viewer. The tool can be used with other types of databases, however, and is not limited to use with contigs or other chemical or biological information and data. Moreover, the tool can be used with any relational data base, particularly (but not exclusively) those that represent data in alphanumeric form.

Figure 8:
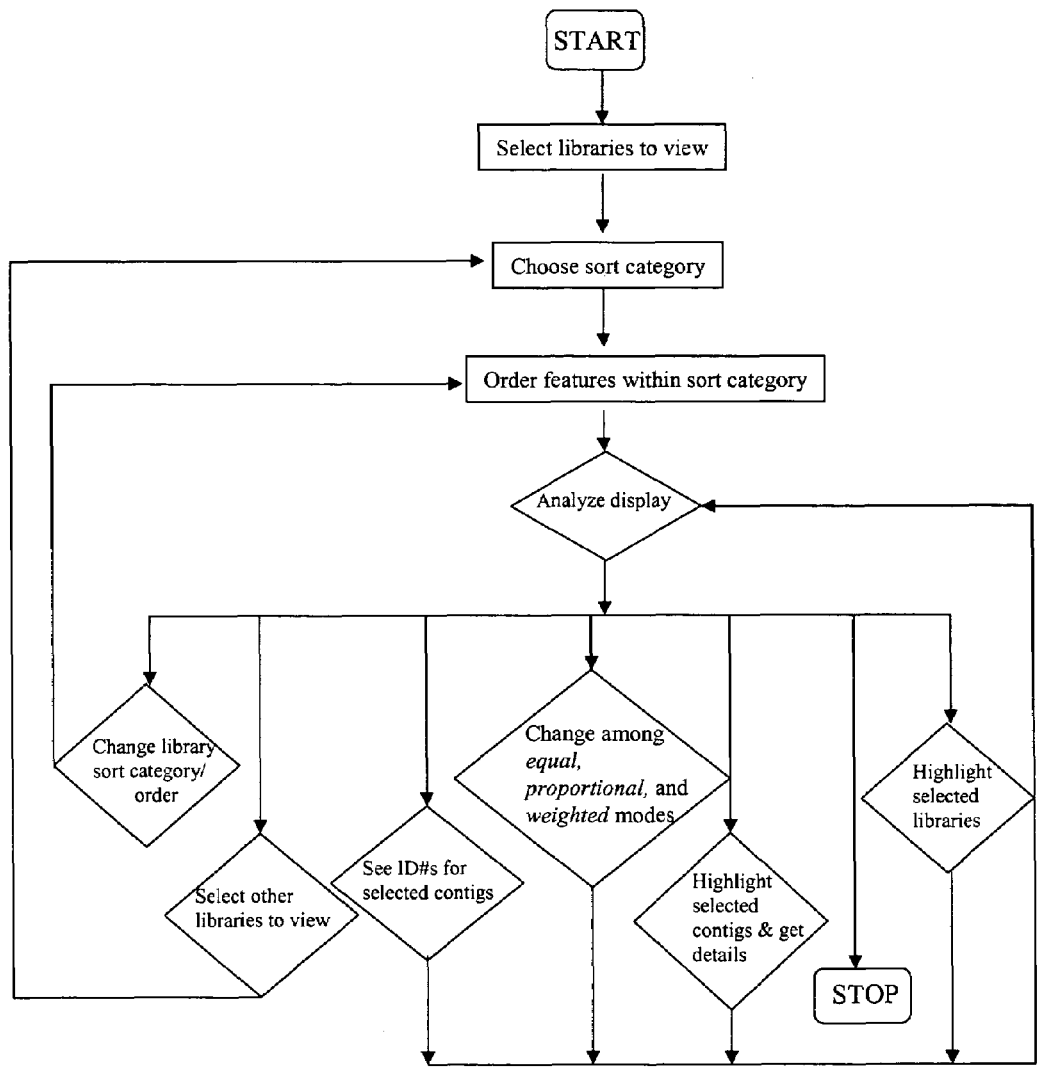
FIG. 8 is a flow chart showing a sample use of the program and the sorting algorithm in respect to various contigs and viewing options such as equal, proportional, and weighted.

FIG. 8 is a flow chart, providing a graphical representation of a sample use of the application.

Appendix 1 is a computer program listing appendix, containing computer programming code.

A sample enablement of the CCV involves use of on-line or downloadable computer programs and databases—in other words, computer programs that are stored on computer-readable media or transmitted by a propagated signal. This illustrative use employs a client/server network, with the Apache, MySQL, and Entrez computer programs installed on a server. Data building is achieved by extracting information from online databases such as NCBI or other sources, and the data can then be parsed using PERL scripts. Entrez is used as a search and retrieval system, identifying files with lists of contigs, component ESTs, and libraries in general. Various java programs and applets may be used, usually with little or no modification. These include, but are not limited to, CViewer.java, DataClient.java, DataServer.java, CtgLibESTServlet.java, Data.java, EstsOfLibrary.java, CreateDB.java, and DBManager.java.

JAVA programs or functions can be used on both the client and server sides of the application. See FIG. 7. The following discussion provides examples of these java applications, programs, and functions on the client side. CViewer.java can serve as a web page for the application. The CViewer class of java application, using GUI for the applet, will provide the following functions: to present initial selection windows and Help frame, to calculate library contributions and x-y plotting coordinates of data clusters/contigs & libraries, to process library and data cluster/contig selections and sort requests, to build strings with info on data clusters/contigs, to display windows from wEST-SQL (another database) with additional data cluster/contig info, to send database queries to DataClient as function calls, to call DataClient objects, and to make use of EstsOfLibrary objects. The DataClient class of java application will implement the data interface serving to: specify option codes for function calls received from CViewer and sending said codes to the CtgLibESTServlet, and by using the EstsOfLibrary objects.

On the server side, several other Java programs or functions can be used or employed. See FIG. 7. These programs include CreateDB, DBManager, DATABASE, DataServer, EstsOfLibrary, and CtgLibEstServlet. These programs can be used for the following functions: CreateDB can be used to load text files using SQL which will include a tally of ESTs for the contig library table, and the call function for DBManager objects; the DataServer java program class can implement various methods such as SQL query strings, relaying queries from the CtgLibESTServlet, can call DBManager objects, and can process EstsOfLibrary objects; and the CtgLibEstServlet can be used for the GET query for connection test, to receive option codes from DataClient, and sending POST data queries using the DataServer connection.

The interface between the client and server is the java TOMCAT program. See FIG. 7.

Together the computer program, its subroutines, and applets provide, inter alia, code segments for receiving input, searching, assigning a value to data clusters which are the result of said searching, and plotting of said clusters in symbol form on a multi-dimensional display which may include color.

The data clusters or contigs are plotted according to a standard x-y coordinate system which is disposed or projected within a usually circular figure appearing on a multi-dimensional graphical display that may selectively include color. The source libraries providing the data for the clusters are each associated with a locus positioned about the periphery of said figure, the number of said loci ("M Loci") corresponding in a one-to-one ratio to the number of data libraries included in the data sort.

The relative (plotting) position of the data clusters is a statistical exercise, in essence using sorting and comparing algorithms to determine degree of relatedness between and among source libraries. The plotting of each symbol within the multidimensional figure is based on a set of coordinates within said multi-dimensional display, wherein said coordinates are a function of a specific comparative analysis applied to said data libraries, namely, the "equal," "proportional," and "weighted" algorithms disclosed herein.

Data sources can be virtually any available data base that provides, in particular, data in alphanumeric form. While the CCV has been used with data related to genomics, it could be adapted for use with relational databases from other fields.

A summary example of the JAVA program set up for data handling is as follows. See FIGS. 7-8, Appendix 1. Program sources are adjustable within the software code to modify the functionality visualized in the display.
- a. Create CViewer2.html web page.
- b. Change estdb variable in DataClient2.java, CtgLibESTServlet2.java, CViewer2.java to correct estdb version in DataClient3.java, CtgLibESTServlet3 java, and Cviewer3 java
  1. Note: These are in /method2/client
  2. &/usr/local/tomcat/webapps/est/WEB-INF/classes
- c. Compile: /usr/java/bin/javac *.java A summary of the mySQL database building steps are:
- a. mysql>INSERT INTO user VALUES("aegilops", "mysql", PASSWOR ("mysqlpw"), "Y", "Y", "Y", "Y", "Y", "Y", "Y", "Y", "Y", "Y", "Y", "Y",
- b. bin/mysqladmin -u mysql -pmysqlpw create estdb;
- c. java CreateDB W_ContigEST_Lib.txt(w/full path) W_Contig_List.txt(w/full path) lib_list.txt(w/full path) RDB estdb mysql(username)
- d. java CreateDB
  /home/nlui/java/Lui/method2/client/NSFT02—Contig EST Lib_fixed.txt
  /home/nlui/java/Lui/method2/client/NSFT02—Contig list.txt
  /home/nlui/java/Lui/method2/client/NSFT02 Lib list_fixed.txt estdb
- e. Change as appropriate for new database(estdb)/file names: mysql
- f. Go into estdb in mySQL (mysql -u mysql -p estdb) to create lib_info table:
  mysql>CREATE TABLE lib info
    ->name varchar(30) NOT NULL PRIMARY KEY
    ->, species varchar(30),
    ->germplasm varchar(40),
    ->tissue varchar(30),
    ->dev_stage varchar(50),
    ->condition varchar(30),
    ->CONSTRAINT lib_fk FOREIGN KEY (name) REFERENCES library(name)
- g. Load the lib_info file:
  mysql>LOAD DATA INFILE'./NSFT02_libinfo_fixed.txt' INTO TABLE lib_info;
- h. Check for and delete null entries:
  DELETE from est WHERE lib_name=" ";
  mysql>delete from lib_info where name=" "; (in case of any blank lines in text file)
  (Optional) Make sure all of the following yield empty sets:
  mysql>select name from contig where name is null;
  mysql>select name from library where name is null;
  mysql>select * from est where name is null;
  mysql>select * from est where ctg_name is null;
  mysql>select * from est where lib_name is null;
  mysql>select * from contig_library where ctg_name=" ";
  mysql>select * from contig_library where lib_name=" ";
  mysql>select * from contig_library where est_number=0;
- i. Shutdown and Restart tomcat data servlet container:
  shutdown.sh and startup.sh when you're done modifying mysql tables.
  Make sure Apache webserver is active.
  Test SQL web services:
  http://machine:8080/est/servlet/CtgLibESTServlet3
  Test applet:
  http://machine:80/CCViewer/Cviewer3.html A summary example of the data building step is set forth below. This data building script will permit the display of data in various settings such as "equal," "proportional," and "weighted."
- a. Collect GI list from Entrez (plant.gi)
- b. gi2url.pl plant.gi>plant.url
- c. wget -a plant.log —O plant.gb -t inf -i plant.url
- d. genbank2ace.pl plant.gb|grep UNHANDLED>plant.log
- e. withlib.pl plant.seq.ace>plant_lib.fasta
- f. fastaclean.pl plant_lib.fasta>plant.fasta
- g. phrap.manyreads plant.fasta -penalty -5-minmatch 50-minscore 75-view>plant.out
- h. phrap2contig.pl plant.view>plant_view.ace
- i. viewcontig.pl plant_view.ace>plant_contig.list [edit contig name]
- j. sort+1 -o plant_contig.sort plant_contig.list
- k. [PREPARE LIBRARY CODE LIST; INTEGRATE INTO BY_LIB.PL]
- l. [CREATE LIBRARY TAB-DELIMITED FILE]
- m. grep Clone_lib plant.seq.ace|sort -u ->plant_code.list
- n. bylib.pl plant.seq.ace>plant_bylib.list
- o. sort -o plant_bylib.sort plant_bylib.list
- p. join -j1-j2 2-o 1.1 2.1 1.2 plant_bylib.sort plant_contig.sort>plant_contig.new
- q. [CREATE TAB-DELIMITED ACCN-CONTIG-LIB LIST]:
- r. space2tab.pl plant_contig.new>plant_contig.tab
- s. create contig list
- t. create library list The data libraries used in this illustration relate to genomics data. EST source information is available to the public, for example, through contributions submitted to the NCBI Genbank resources, and much of the illustrative Triticeae EST information disclosed herein is available at the GrainGenes project site (Matthews et al., 2003, GrainGenes, the Genome Database for Small-Grain Crops, Nucleic Acids Research 31:183-186). Moreover, these sequences have been applied to Triticeae genomics in a wide variety of ways, including the development of molecular markers, placement on physical and genetic maps, characterization as gene candidates, and used for comparative studies between related species (Sorrells et al., 2003, Comparative DNA Sequence Analysis of Wheat and Rice Genomes, Genome Research).

Figure 2:
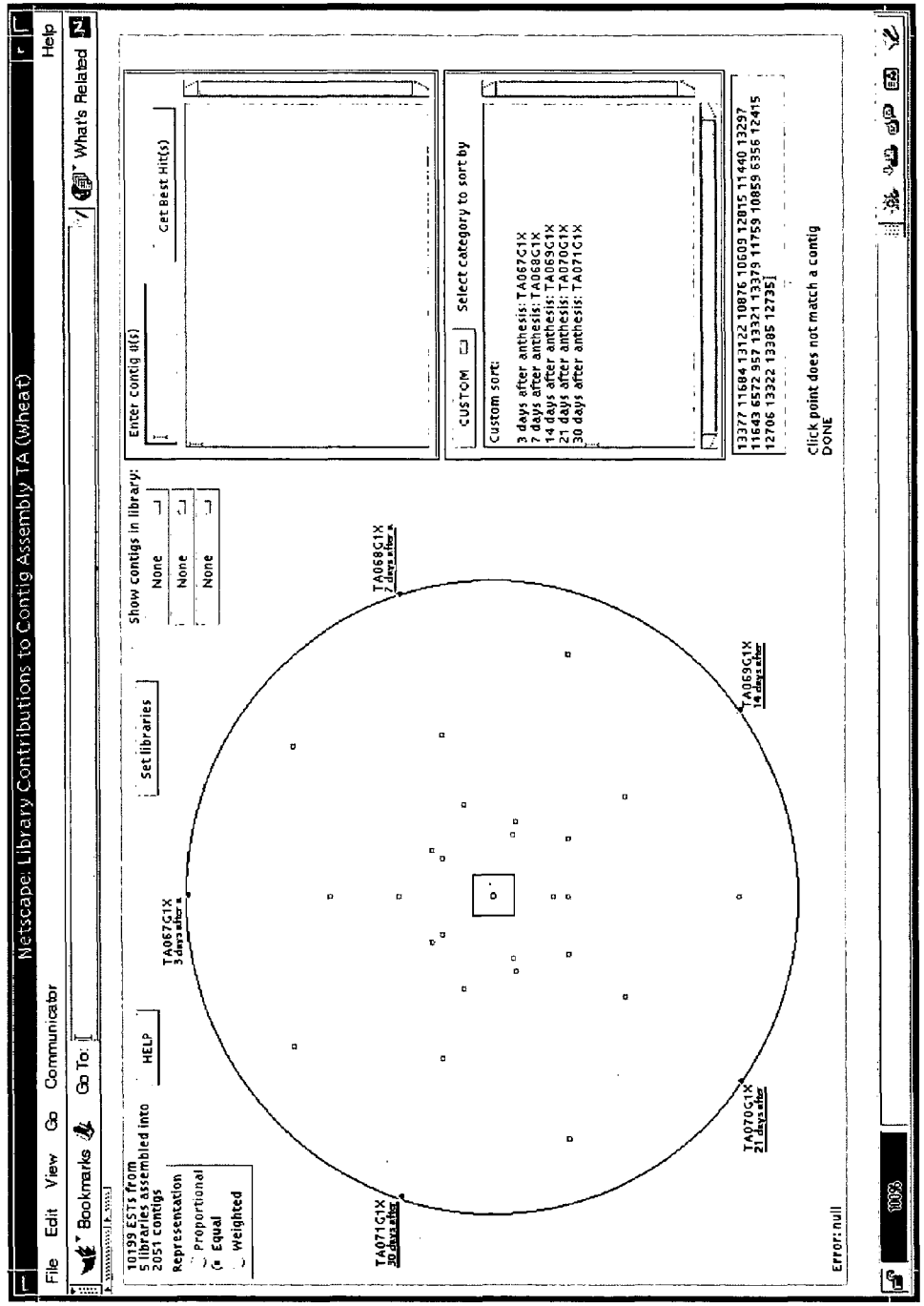
FIG. 2 is a representation of the graphical display showing contigs from five separate libraries in the "equal" setting. The rectangle around the center contig point has been selected using a "mouse" device to highlight the points which have EST members from all libraries around the periphery. In this "equal" setting, intersecting points between libraries represent the EST members contributing to the contig point. In the example provided, point identifiers are listed in the text box located in the lower right area of the display. The display as represented is a "snapshot" and not all of the point identifiers in the text box appear in this particular view—they do become visible in a dynamic environment when the mouse device is used to activate or scroll through them.

In "equal setting," the symbols representing contigs are placed within the display in respect to the libraries contributing ESTs to contigs (FIG. 2). The placement of the contigs is on an x-y axis and represents a clear mid-point cross-section between all libraries contributing at least one EST to the assembled contigs. If every library represented in the display had at least one EST member in a particular contig, that contig would be placed at the center point of the multi-dimensional color display as shown in FIG. 2.

Figure 3:
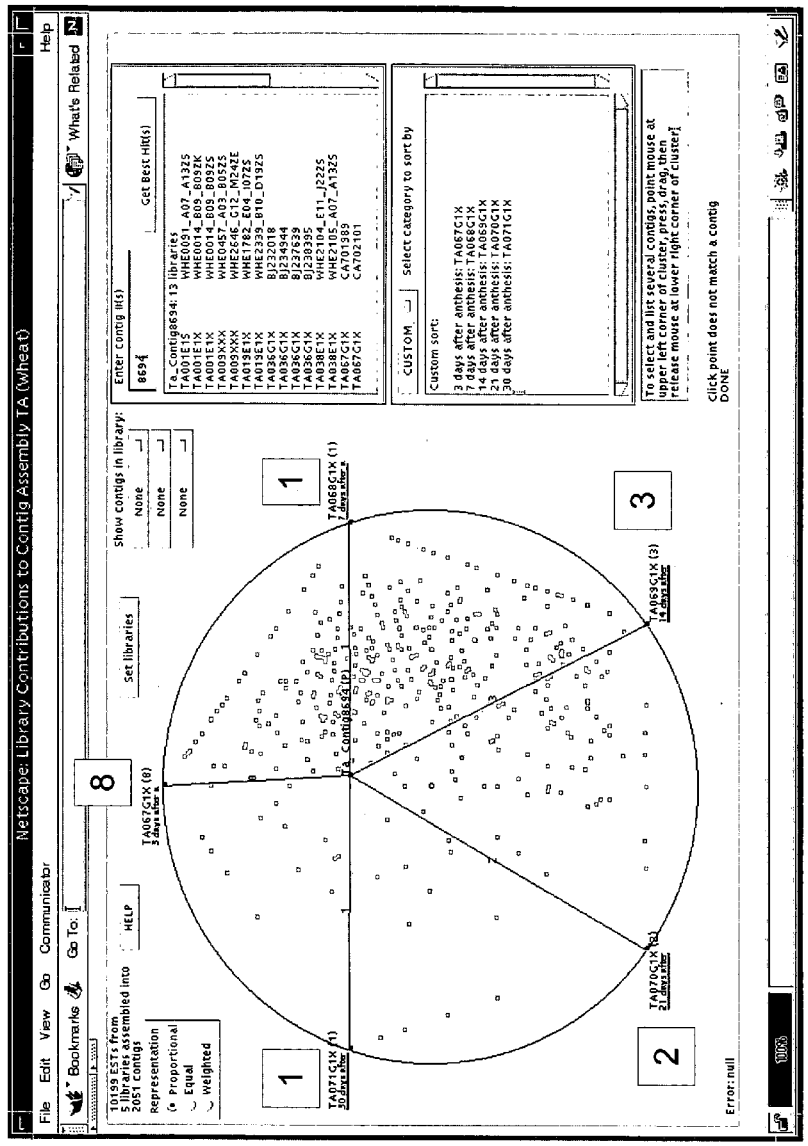
FIG. 3 is a representation of the graphical display showing contigs from the same five libraries as in FIG. 2, but displayed in the "proportional" setting.

In "proportional setting," the contigs or data clusters are placed in the display figure with respect to the number of EST members from a given library represented in a contig (FIG. 3). If a single library contributed proportionally 0.5, or one half, of the ESTs clustered into a contig, the contig point would migrate 0.5 of the distance, between the relevant libraries, towards the direction of the represented library. Similarly, the other library influences on point migration would be determined by the proportional representation of the other libraries in the contig.

Figure 4:
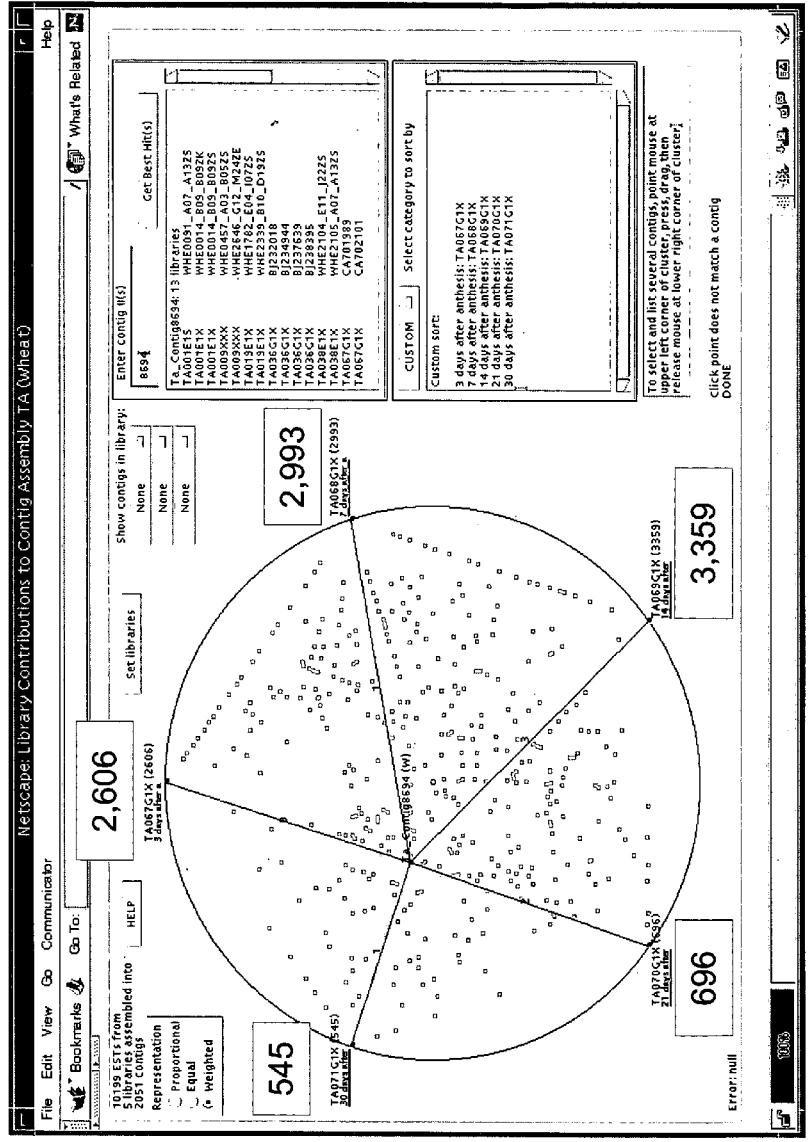
FIG. 4 is a representation of the graphical display showing contigs from the same five libraries as in FIG. 2 (and FIG. 3), but displayed in the "weighted" setting. The numbers highlighted around the periphery indicate the total number of data sequences available from each library. From contig point 8694, lines radiate to the libraries which contributed to that point and show the numbers from each library so contributing; other points remain as non-annotated points. In the actual display, the number of sequence data available from each library name would appear in parentheses, and along the radiating lines to the connecting libraries.

"Weighted setting" is much like the Proportional setting in that the number of ESTs contributing to the contig is important. (FIG. 4). However, to account for contributions from libraries from which few ESTs were sequenced, the contig point migration is adjusted based on fractional or percentage representation of the ESTs from a given library (FIG. 4). For instance, a single contig with ESTs derived from two libraries, consisting of one EST from library A and nine ESTs from library B, would be located midpoint if library A had a total of 100 sequences and library B had a total of 1,000; both libraries would be given a weighted value of 0.01, each representing about one percent of the library in the contig.

The above are only three settings among many possible options. Such options would depend, in part, on the sorting algorithms used in order to provide different graphical perspectives.

Discerning contig-attribute relationships can also be illustrated by example.

Because libraries represented in the CCV display can be sorted based on key library components, or attributes, the data can be manipulated or displayed in a way that shows which contigs (and by inference which libraries) associate with these key attributes. Since contigs patterned as simple intersections between libraries may not adequately explain contig-component relationships, other algorithm settings can be used. The following are a few examples representing a range of applications.

Figure 5A:
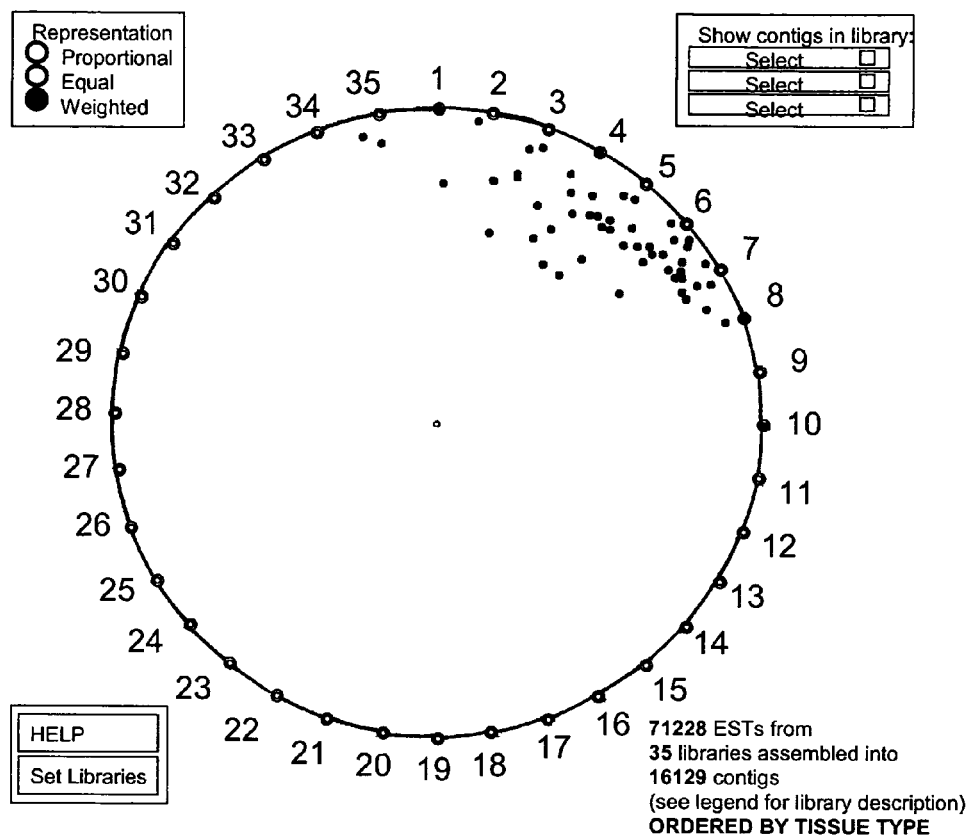
FIGS. 5A and 5B show the plot distribution of a data set with the libraries rearranged differently around the periphery of the display. The data set in this example shows 16,129 contig data points from 35 libraries which collectively contain 71,228 EST members.

The ordering of the libraries within the CCV display by tissue attributes makes it possible to detect contigs that may be strongly associated with specific tissues. See FIG. 5(a). Sorting the libraries by tissue could be useful when a researcher is focusing on contigs associated with tissue-specific expression or when hunting for genes that may carry tissue-specific promoters. As an example, *Fusarium* head blight is a serious disease threat to the Triticeae agricultural crops, primarily affecting the flowering parts of the plant. Attempts at constructing or studying potential resistance mechanisms are focusing on expression in the spike tissues. The sorting of spike and closely related tissues together in the CCV display facilitates analysis of those contigs highly associated with those tissues.

Figure 5B:
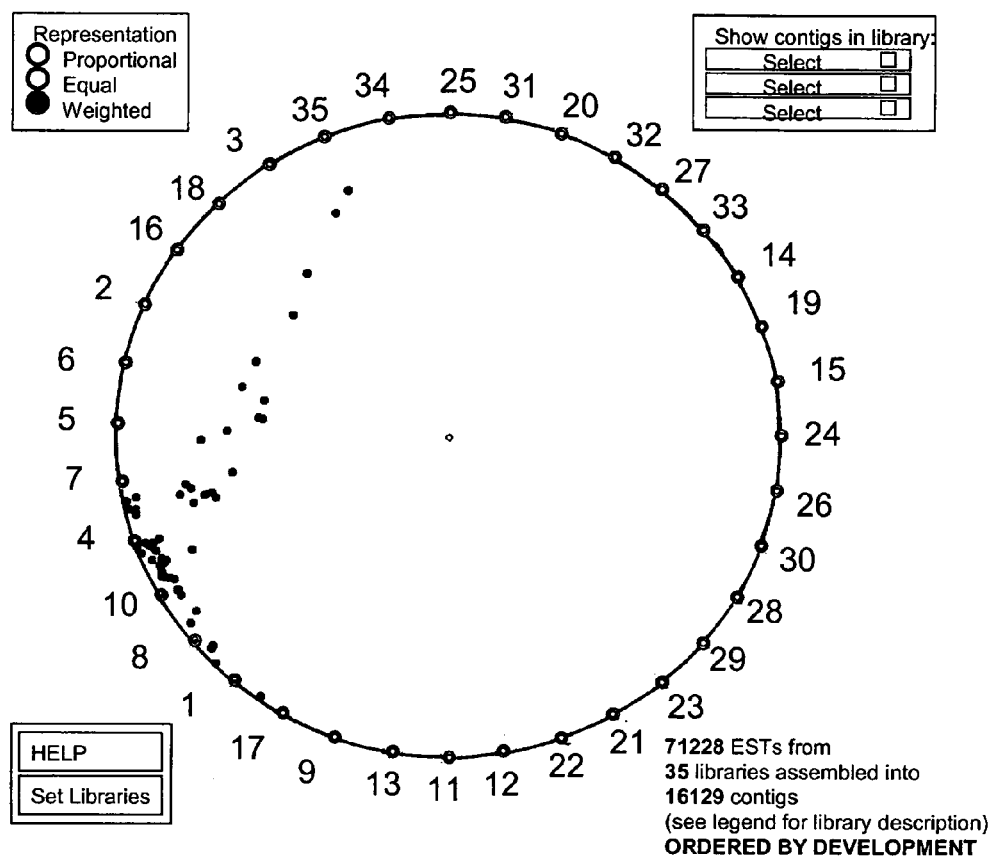

Contigs may also be sorted according to their developmental expression. See FIG. 5(b). A single assembly may involve constructing contigs from sequences derived from a wide range of libraries; for example, there are about 152 different cDNA libraries constructed for *T. aestivum*. In some cases, cDNA libraries can be constructed to cover a very distinct set of developmental stages, for instance: 3, 7, 14, 21, and 30 days after anthesis for the developing kernel (Tingey et al., 2003, EST Libraries wdk1c, wdk2c, wdk4c, and wdk5c, deposited at NCBI dbEST, www.ncbi.nlm.nih.gov/dbEST). Displaying only a subset of these five libraries allows a visualization of contigs associated with each stage of development, as well as those constitutively expressed. Visualizing the contigs in this fashion allow for stepwise selection of contigs specifically associated between incremental steps. Likewise, such a collection could also be compared to libraries for which several time points may have been pooled. The ability to study library subsets, depending on the range of stages from which libraries have been constructed leads to the opportunities to study developmental traits relating to flowering, nutrition, resistance/susceptibility, among other potential quantitative traits.

Treatment Differentiation. Many cDNA libraries have been constructed primarily to distinguish differences in expression between different conditions, and a variety of methods have been developed to exploit these differences (e.g. differential display, microarrays, subtractive hybridization). The CCV display can be adjusted to pool different treatments and match them up against controls. There are publicly available libraries that have been constructed against a range of pathogens and environmental stresses allowing the possibility to categorize genes associated with different conditional states of the plant.

Germplasm Differentiation. There may be situations where a comparison between different germplasm may explain the differences in gene expression. It may be possible to identify genes responsible for quality phenotypes, disease resistance, or differential expression due to nutrition or stress conditions. In cases where phenotypes are multigenic, a family of genes associated with a quality trait might be determined. The CCV display allows for the sorting of assembled genes that are shared or differentiated by germplasm.

As contigs can be assembled to differentiate germplasm, such as by cultivar characteristics; the same display can also be used to differentiate germplasm by species. Depending on the stringency of the assembly it may be able to distinguish between genes shared, or highly similar between germplasm and species. The general observation was that the species were quite distinct, but there were many instances where the contigs formed contained and shared ESTs derived from both species.

Figure 6:
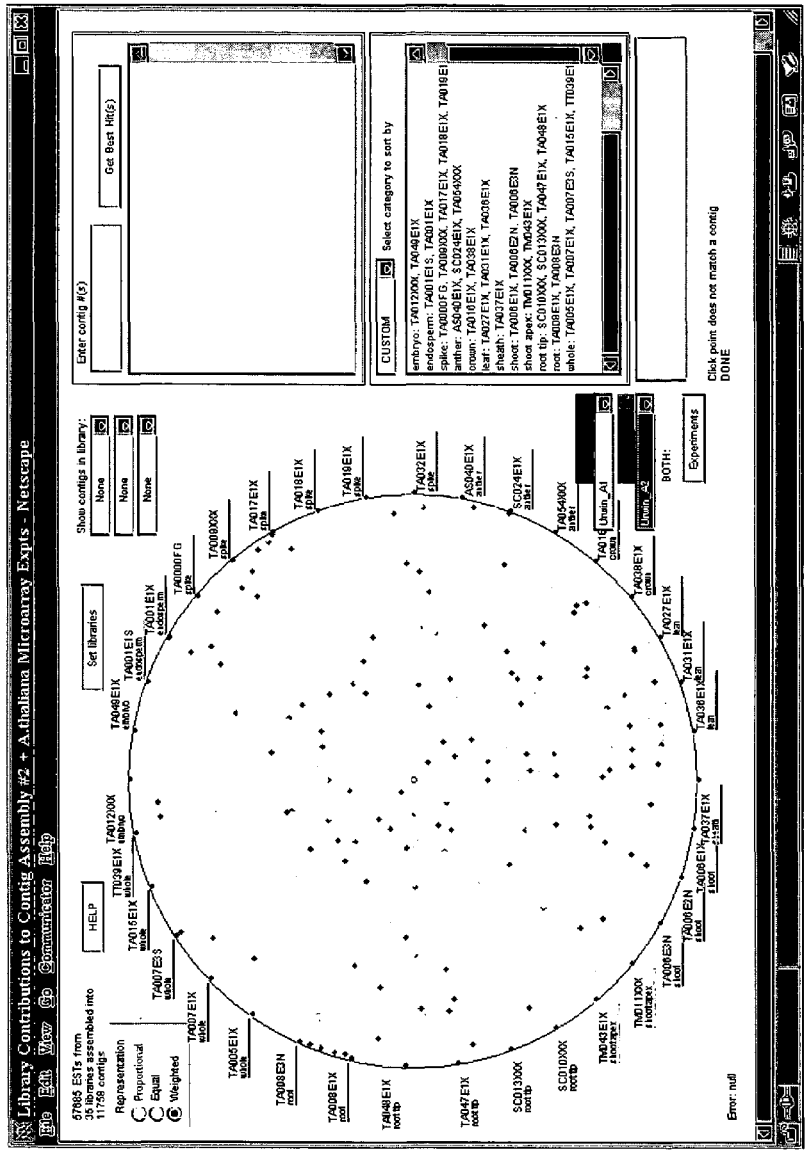
FIG. 6 is an extended application of the CCV program used to display microarray data superimposed onto contig assembly data. In the example, two experiments, a CONTROL experiment and a TEST experiment, are displayed. Contig data points displayed in "yellow" represent expressed signals in both the CONTROL and the TEST experiments. Contig data points highlighted in "red" represent instances in which the CONTROL sequence is expressed, but not the TEST, and points highlighted in "green" represent instances in which the TEST experiment sequence to be expressed and not the CONTROL. The relative intensity of "green" or "red" are calibrated from raw data from the microarray experiment. A separate protocol is used to prepare this data for entry into the mySQL relational database.

Microarray Comparison. Microarray technology is rapidly becoming a primary means for measuring gene expression due to capabilities to use high throughput means to create the arrays and the ability to screen thousands of genes at one time (Fellenberg et al., 2001, Li, 2001). The probes used to screen against microarrays are similar to the building of cDNA libraries in that the probe material is derived from the isolation of mRNA under a specified set of conditions. Microarray studies are just now under development for study within the Triticeae species; however, to facilitate the study of microarray expression analysis, the CCV display tool was initially set up to read currently available data sets to perform mock microarray analysis without the costly production of microarrays or building of RNA probes. For instance, microarray experiments for the model organism *Arabidopsis thaliana* was used for study and compared against a *T. aestivum* contig assembly. See FIG. 6. In this case, the Triticeae contigs were matched to microarray probe sequences using different threshold cutoff values. See FIG. 6. Also added was a false-coloring overlay to give an appearance similar to that associated with microarray analysis software. See FIG. 6. Though the data is derived from another species, this feature may assist in pointing to previously documented genes for which expression is somewhat understood and may point to new or unrealized gene relationships based on expression profiles and clustering.

Assembly Comparison. For phylogenetic studies, a series of stepwise calculations can be performed to build independent data assembly sets; migration of clusters, or changes in the cluster members can be analyzed to determine sequence, or phylogenetically-dependent associations. Given another assembly, it may be possible to distinguish sequences that are genome specific from within a polyploid environment. For instance, T. aestivum is a hexaploid species having genome content from the A, B, and D genomes. Using a combination of hexaploid, tetraploid, and diploid species the display set would be sorted by species to observe genome-specific clustering. By comparing different assembly methods, patterned changes in clustering may lead to develop observations on genome evolution as determined by cluster formation.

Other comparisons and applications are also possible, depending on the availability of data.

Through the assembly method, for example, several representatives of a gene class may be present in the display which may represent duplication of related sequences; this is especially so in a polyploid organism. A simple query will show the placement of the related sequences as distributed with the sorting criterion. A follow-up analysis of the contigs formed may point to the cause of contig divergence, possibly due to sequence evolution and formation of homologies due to duplications or rearrangements. Or it may simply be the lack of closing a gap between 5' and 3' sequences. However, by a thorough study of contig placements within the CCV display, it may be possible to develop theories of gene adaptation, which can be associated with certain tissues, or stages of development.

With respect to the sorting criterion, contig-component relationships may be displayed to relate clustering, or scattering. For instance, one may be interested in how specific pathway-associated sequences are related to the libraries displayed. By loading a list of identified pathway-classified contigs, only those contigs can be highlighted and can relate candidate function to map position, metabolic pathway, or other general interest queries. In some cases this is useful for assessing the quality of the library. If the library was from a subtracted or normalized library, the treatment can be easily compared to one that was not treated. This is sometimes useful for determining if the library is yielding additional unique sequences, or if the general background signals are being minimized.

Other applications of the display tool are possible, depending primarily on the availability of relational databases containing alphanumeric data.

What is claimed is:

1. A method for displaying contig-component relationships comprising:
    a. providing EST data from a plurality of EST source libraries wherein, the EST data comprises: ESTs, their library of origin, and their membership in an assembled contig;
    b. providing a multi-dimensional display comprising a circular figure, wherein,
        loci representing each source library comprising the plurality of EST source libraries, are distributed about the periphery of the circular figure;
    c. assembling contigs by removing EST redundancy, and aligning and clustering ESTs that comprise the plurality of EST source libraries, using an assembly algorithm, thereby producing assembled contigs;
    d. plotting at least one symbol within the multidimensional display, corresponding to at least one assembled contig, wherein the at least one symbol is positioned within the multidimensional display according to relative contributions of ESTs from the source libraries used to assemble the at least one contig;

thereby displaying contig-component relationships by positioning the at least one symbol corresponding to the at least one assembled contig within the multi-dimensional display, at a point within an area located between the loci representing the EST source libraries that contributed to assembly of the at least one contig.

2. The method of claim 1, wherein positioning the at least one symbol corresponding to the at least one assembled contig within the multidimensional display, is determined as a function of the number of source libraries which contributed at least one EST to the at least one assembled contig.

3. The method of claim 1, wherein positioning the at least one symbol corresponding to the at least one assembled contig within the multidimensional display is determined as a function of the proportion of ESTs in the at least one assembled contig that are contributed by each source library.

4. The method of claim 1, wherein positioning the at least one symbol corresponding to the at least one assembled contig within the multidimensional display is determined as a function of the number of ESTs in the at least one assembled contig from a given source library relative to the total number of ESTs in the source library.

5. The method of claim 1, wherein source libraries are members selected from the group consisting of source libraries comprising EST data from: a species, a cultivar, a tissue, a developmental stage, and a stress condition or a combination of such members.

6. The method of claim 1, wherein the method is used to perform mock microarray analysis.

7. The method of claim 1, wherein positioning the at least one symbol corresponding to the at least one assembled contig within the multidimensional display is influenced by the placement of the of the source libraries about the periphery of the circular figure.

8. A computer readable storage medium having computer program for displaying contig-component relationships stored thereon, wherein the computer program for displaying contig-component relationships comprises:
    a. a receiving code segment;
    b. an assigning code segment; and
    c. a plotting code segment
    wherein the computer program causes a computer to:
    (i) utilize EST data from a plurality of EST source libraries to assemble contigs by removing EST redundancy, and aligning and clustering ESTs comprising the plurality of EST source libraries using an assembly algorithm thereby producing assembled contigs; and
    (ii) plot at least one symbol corresponding an to at least one assembled contig within a multidimensional display comprising a circular figure, wherein
    the at least one symbol is positioned within the multidimensional display according to relative contributions of ESTs from the source libraries used to assemble the at least one contig; thereby positioning the at least one symbol corresponding to the at least one assembled contig within the multi-dimensional display, at a point within an area located between the loci representing the EST source libraries that contributed to assembly of the at least one contig.

* * * * *